United States Patent [19]

Turner et al.

US005391629A

[11] Patent Number: 5,391,629
[45] Date of Patent: Feb. 21, 1995

[54] BLOCK COPOLYMERS FROM IONIC CATALYSTS

[75] Inventors: Howard W. Turner, Webster; Gregory G. Hlatky, Houston; Henry W.-H. Yang, Kingwood; Avinash C. Gadkari, Webster; Gary F. Licciardi, Humble, all of Tex.

[73] Assignee: Exxon Chemical Patents Inc., Linden, N.J.

[21] Appl. No.: 35,021

[22] Filed: Mar. 22, 1993

Related U.S. Application Data

[63] Continuation-in-part of Ser. No. 477,791, Feb. 9, 1990, abandoned, which is a continuation-in-part of Ser. No. 133,052, Dec. 21, 1987, abandoned, and a continuation-in-part of Ser. No. 133,480, Dec. 22, 1987, abandoned, which is a continuation-in-part of Ser. No. 8,800, Jan. 30, 1987, abandoned, said Ser. No. 133,052, is a continuation-in-part of Ser. No. 11,471, Jan. 30, 1987, abandoned.

[51] Int. Cl.⁶ .................. C08F 4/76; C08F 297/08
[52] U.S. Cl. .................... 525/268; 525/321; 525/323
[58] Field of Search .................. 525/268, 321, 323

[56] References Cited

U.S. PATENT DOCUMENTS

| 4,141,847 | 2/1979 | Kiovsky . |
|---|---|---|
| 4,408,019 | 10/1983 | Blunt . |
| 4,481,336 | 11/1984 | Fuji . |
| 4,522,982 | 6/1985 | Ewen . |
| 4,849,487 | 7/1989 | Kaminsky . |
| 4,959,436 | 9/1990 | Cozewith . |

FOREIGN PATENT DOCUMENTS

| 041361 | 12/1981 | European Pat. Off. . |
|---|---|---|
| 277003 | 8/1988 | European Pat. Off. . |
| 0277003 | 8/1988 | European Pat. Off. . |
| 277004 | 8/1988 | European Pat. Off. . |
| 0277004 | 8/1988 | European Pat. Off. . |
| 426637 | 5/1991 | European Pat. Off. . |
| 426638 | 5/1991 | European Pat. Off. . |
| 427696 | 5/1991 | European Pat. Off. . |
| 427697 | 5/1991 | European Pat. Off. . |
| 3640924A1 | 6/1988 | Germany . |
| 3826075A1 | 2/1990 | Germany . |
| 601506 | 2/1960 | Italy . |
| 63-063712 | 3/1988 | Japan . |
| 895769 | 7/1989 | South Africa . |

OTHER PUBLICATIONS

Kunstoff–Handbuch Band IV *Polyolefin;* Carl Hanser Verlag, Munchen 1969.
Vollmer, B. Makromolekularen Chemie; E. Vollmer, Verlag, Karlsruhe 1989 pp. 203–204.
Encyclopedia of Polymer Science and Engineering; pp. 437–445 1986.
Falk & Scott, Macromolecules, 1971, 4, 152.
Doi, et al., Macromolecules, 1986, 19, 2896.
Kaminsky & Sinn, "Transition Metals and Organometallics as Catalysts for Olefin Polymerizations", Springer–Verlag, 1988.

*Primary Examiner*—Vasu S. Jagannathan
*Attorney, Agent, or Firm*—C. L. Bell; M. B. Kurtzman; M. S. Spiering

[57] ABSTRACT

A process for the production of block copolymers of ethylene and an α-olefin such as propylene by using an ionic catalyst system including a metallocene component and a component having a cation capable of donating a proton and a compatible non-coordinating anion. Novel block copolymers are produced.

11 Claims, 3 Drawing Sheets

BLOCK COPOLYMERS FROM IONIC CATALYSTS

CROSS-REFERENCE TO RELATED APPLICATIONS

This application is a continuation in part of U.S. Ser. No. 477,791, filed Feb. 9, 1990, which is a continuation-in-part of U.S. patent application Ser. Nos. 133,052, filed Dec. 21, 1987, and 133,480, filed Dec. 22, 1987, U.S. patent application Ser. No. 133,052, is in turn a continuation-in-part of U.S. patent application Ser. No. 011,471, filed Jan. 30, 1987, U.S. patent application Ser. No. 133,480, is in turn a continuation-in-part of U.S. patent application Ser. No. 008,800, filed Jan. 30, 1987, all of which are incorporated by reference, all now abandoned. This application is also related to copending U.S. Ser. No. 07/917,008.

FIELD OF THE INVENTION

This invention relates to a method for preparing block and tapered copolymers by polymerizing ethylene and other olefins in the presence of an activated cyclopentadienyl transition metal catalyst system. More particularly, this invention relates to a process for the production of multiblock and tapered copolymers of ethylenically unsaturated monomers. The invention also related to the multiblock and tapered copolymers produced.

BACKGROUND OF THE INVENTION

Block copolymers are well known and have been used commercially as components in adhesives, as melt processable rubbers, impact resistant thermoplastics, and as compatibilizers, or "surfactants", for emulsifying polymer-polymer blends.

A block copolymer is created when two or more polymeric segments, or blocks, of different chemical composition are covalently bonded in an end-to-end fashion. Block copolymers have certain advantages over blends. Firstly, the segments are covalently bonded to each other, thereby eliminating the interface problem. Secondly, block copolymers can be used to strengthen blends of immiscible polymers by serving as "emulsifiers," which encourage physical connections between the phase, and thus improve the interfacial adhesion and load transferring capability of the components.

While a wide variety of block copolymer architectures are possible, most block copolymers of interest involve the covalent bonding of hard plastic segments which are crystalline or glassy, to elastomeric blocks forming thermoplastic elastomers. Other block copolymers, such as rubber-rubber, glass-glass, and glass-crystalline block copolymers are also possible and may have commercial importance. Two common types of block copolymer structures are the diblock and triblock forms. However, multiblock copolymers, in which more than three segments are bonded together, are also desirable.

Block copolymers are similar to, yet distinct from, tapered polymers. In a tapered copolymer the composition of comonomer is gradually varied from one end of the polymer to the other. Tapered copolymers are commercially used as viscosity modifiers, oil additives, thermoplastic elastomers, and impact-resistant plastics.

Block copolymers have been made by anionic polymerization routes. Butadiene-isoprene block copolymers have been synthesized using the sequential addition technique. In sequential addition, a certain amount of one of the monomers is contacted with the catalyst. Once the monomer has reacted to extinction, forming the first block, a certain amount of the second monomer species is introduced and allowed to react to form the second block. The process may be repeated as desired using the same or other anionically polymerizable monomers.

Likewise, olefin based block copolymers have not been successfully synthesized through coordination catalysis. Several difficulties arise in the use of known coordination catalysts for the block copolymerization of olefins. Among those are the fact that conventional catalysts are typically multi-sited, and a significant fraction of the active sites are unstable. This leads to random chain initiation and termination which, in turn, lowers the theoretical block copolymer yield. What is desired, and what practice of this invention provides, is a catalyst system with well-characterized structure and reactivity which has a single active site. The system should have well-defined and stable polymerization kinetics and be free of aluminum alkyls or other chain transfer agents.

SUMMARY OF THE INVENTION

The invention comprises a process for the production of novel block copolymers of ethylene with an α-olefin and the polymers obtained therefrom. The process includes sequentially contacting ethylene with an α-olefin monomer in a suitable solvent at about 0° C. in the presence of an activated cyclopentadienyl catalyst system to produce a block or tapered block colpolymer. The activated catalyst will polymerize α-olefins to form tapered polymers and multiblock polymers such as di- and tri-block homopolymers and copolymers of ethylene and propylene with one or more other alpha-olefins.

DESCRIPTION OF PREFERRED EMBODIMENTS

Figure 1:
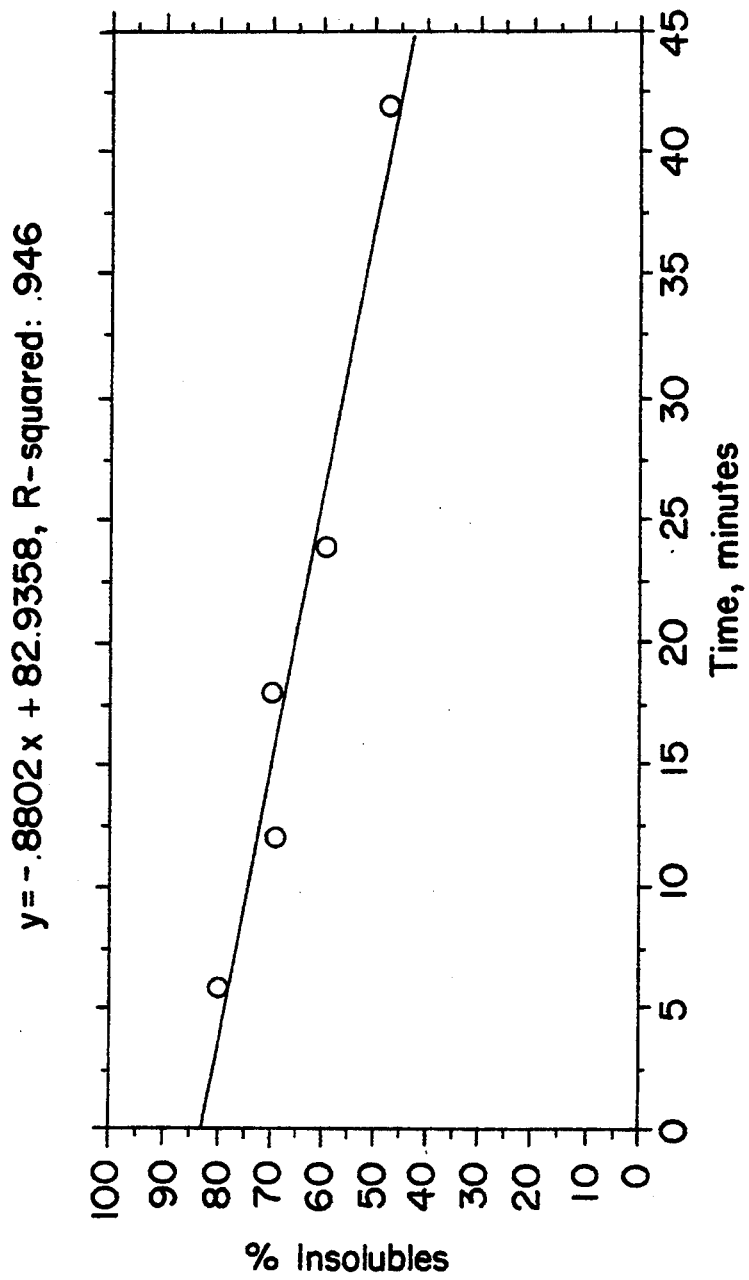
FIG. 1 is a graph of the percent insolubles vs polymerization time in minutes.
Figure 2:
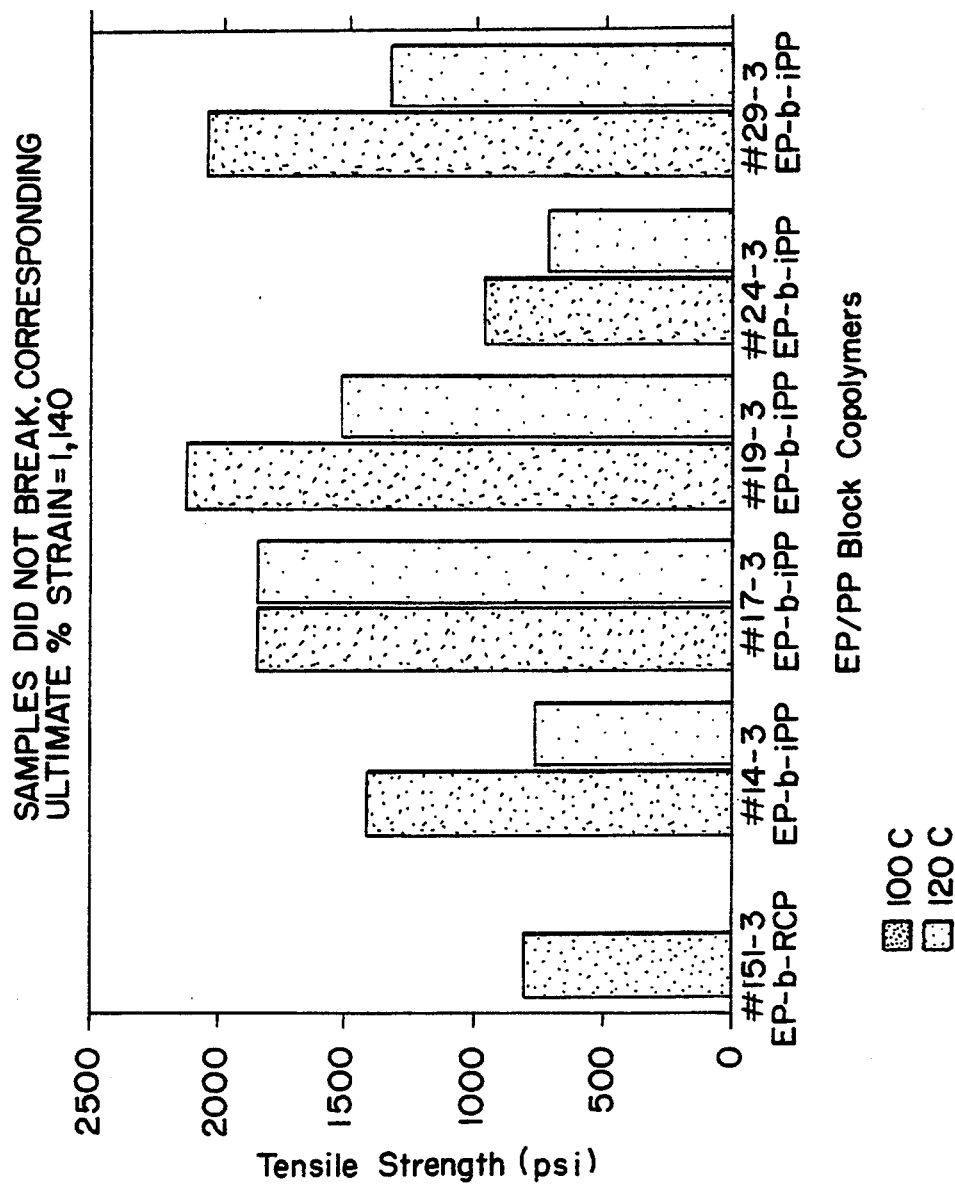
FIG. 2 is graph of the tensile strength of EP/PP block copolymers at 100 and 120 degrees C.
Figure 3:
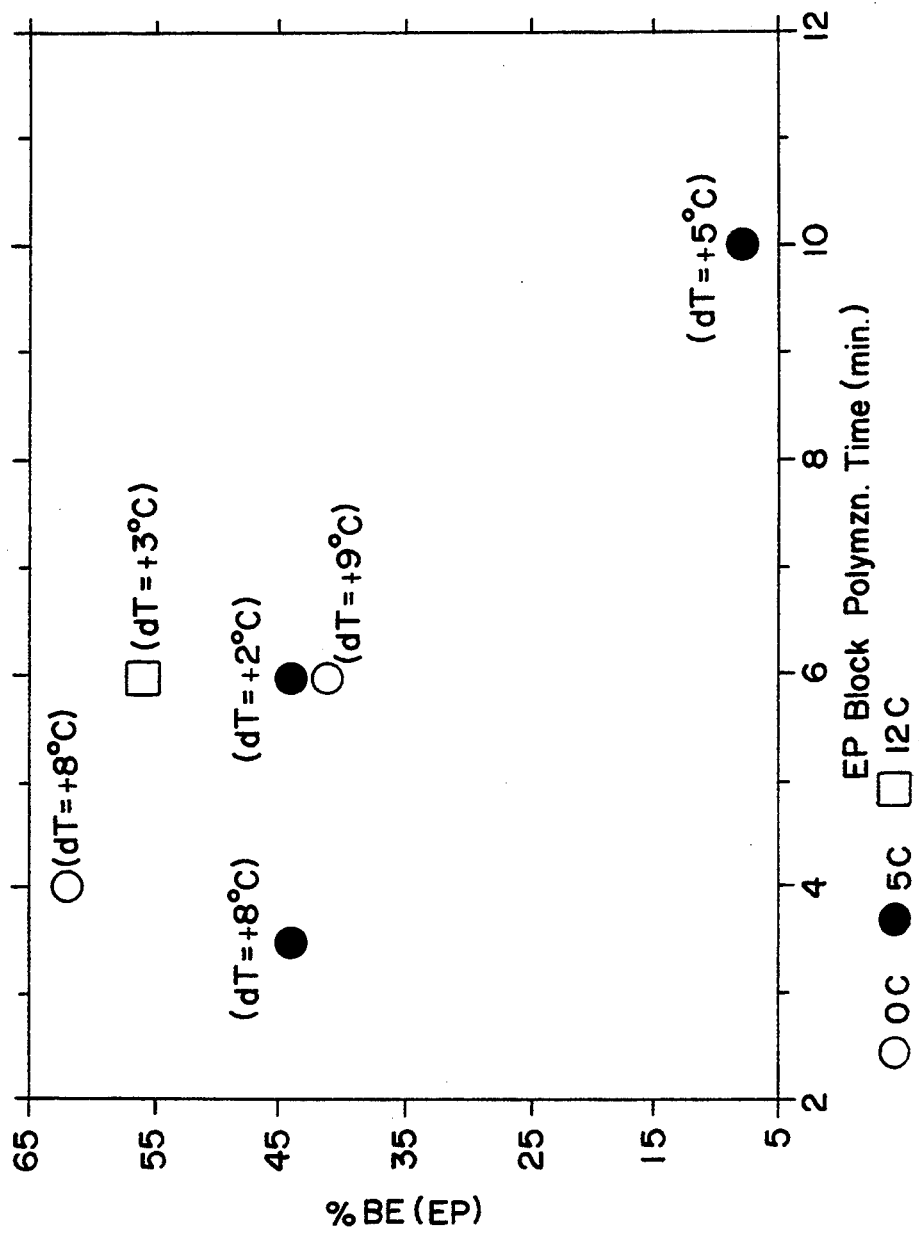
FIG. 3 is a graph of the effect of EP—block polymerization time on blocking efficiency.

The invention provides (1) novel di, tri-, and multiblock copolymers and tapered copolymers of ethylene, 1-olefins, diolefins, cyclic olefins, acetylenes and other unsaturated monomers; and (2) the processes for polymerizing said block copolymers.

Activated Catalyst System—General System

The process of this invention is practiced with that class of catalyst referred to, disclosed, and described in U.S. Pat. Nos. 5,055,438; 5,057,475; 5,096,867; 5,017,714; 5,153,157; copending U.S. Ser. Nos. 542,236 filed Jun. 22, 1990; 468,382 filed May 21, 1991; 885,170 filed May 18, 1992; 737,611 filed Jul. 19, 1991; 926,006 filed Aug. 5, 1992; 07/133,052 and 07/133,480 and EPA's 277,003, 277,004, published Jun. 3, 1988; EPA 129,368 published Dec. 22, 1984, EPA 520,732 published Dec. 30, 1992 all of which are incorporated by reference herein. The activated catalyst is prepared by combining at least two components. The first of these is a mono or bis(cyclopentadienyl) derivative of a Group IV-B metal compound containing at least one ligand which will combine with the second activator component or at least a portion thereof such as a cation portion thereof. The second component may be an alumoxane or a noncoordinating anion.

Choice of Group IV Metal Component

In general, most Group IVB metal components may be combined with most activator components to produce an active olefin polymerization catalyst.

To obtain block copolymer with a hard segment and a soft segment, it is important to choose a catalyst capable of producing both. For example, a chiral activated catalyst will produce stereoregular polyolefins while an achiral activated catalyst typically produces non-stereoregular, even amorphous polyolefins. As an example, a chiral cyclopentadienyl hafnium based catalyst could be used to produce hard blocks of isotactic polypropylene and at different reaction conditions the same catalyst could then produce soft "elastomer" blocks of EP. Anionic coordination complexes containing perfluorphenyl-, trifluoromethylphenyl-, or bis-trifluormethylphenyl rings are preferred. When the non-coordinating anion contains a plurality of boron atoms, more effective catalysts are obtained with activator compounds containing larger anions.

Preferred Catalysts for the Production of Block and Tapered Copolymers

Preferred catalyst systems for the production of block copolymers are single-sited living catalysts. Living catalysts are those systems in which chain transfer is substantially nonexistent and the rate of initiation is fast compared to propagation. Catalysts which have finite chain transfer rates may also be useful for the production of block and tapered copolymers if the rate of propagation is fast relative to termination. It is also important that the average chain lifetimes are reasonably long (minutes to hours) in order to permit adequate time for modifications of the reactor conditions (e.g. changing monomer feed streams). While most reasonably stable ionic catalysts described above will under suitable conditions produce block and/or tapered copolymers of nonpolar olefins, it is preferred that the catalyst be: 1) thermally stable (recoverable as a single organometallic complex), 2) versatile in terms of random copolymer synthesis (i.e. capable of preparing HDPE, i-PP, s-PP, EP-rubber, LLDPE etc.), 3) capable of producing high molecular weight polymers at reasonable temperatures and pressures, 4) high activity (fast propagation catalysts) and 5) slow in chain termination reactions so that few chains of polymer product are produced per hour per site.

Preferred activated biscyclopentadienyl catalysts are represented by the formulae:

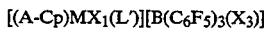

wherein: M is titanium, zirconium or hafnium; (A-Cp) is either $(Cp)(Cp^*)$ or $Cp-A'-Cp^*$; and Cp and $Cp^*$ are the same or different substituted or unsubstituted cyclopentadienyl radicals; $A'$ is a covalent bridging group containing a Group IV-A element; $L'$ is a neutral Lewis base; $X_1$ is a hydride radical, hydrocarbyl radical having from 1 to about 20 carbon atoms, substituted-hydrocarbyl radical, wherein 1 or more of the hydrogen atoms are replaced with a halogen atom, having from 1 to about 20 carbon atoms, or organo-metalloid radical comprising a Group IV-A element wherein each of the hydrocarbyl substituents contained in the organo portion of said organo-metalloid, independently, contain from 1 to about 20 carbon atoms; $X_3$ is a hydride, halide, hydrocarbyl radical, a $C_1$-$C_{20}$ hydrocarbyl radical wherein one or more of the hydrogen atoms is replaced by a halogen atoms, organometalloid radical wherein each hydrocarbyl substitution in the organo portion contains from 1 to 20 carbon atoms and the metal is a Group IVA metal and $B'$ is a noncoordinating anion. In another preferred embodiment $B'$ can be replaced with an alumoxane, preferrably methylalumoxane. These catalysts are preferred catalysts for the production of block and tapered copolymers of ethylene, 1-olefins, dienes, cyclic olefins and other unsaturated monomers. Ionic catalysts of this form where M=Hf are the most preferred. Polymerizations using hafnium systems of this form under standard random copolymer conditions as described in our copending U.S. patent application Ser. No. 133,480 produce high molecular weight HDPE, LLDPE, a-PP, i-PP, s-PP, and EP-rubber at rates comparable to similar Zr-based catalysts. In another embodiment on of the Cp rings could be replaced by a heteroatom ligand as described in U.S. Pat. No. 5,055,438, incorporated by reference above. Tapered and block copolymers containing the above segments can be produced using the appropriate hafnium ionic catalysts using the techniques and process conditions set forth in the following sections.

Processes for the Production of Block and Tapered Copolymers

Many procedures for modifying the reactor conditions and monomer feeds for the production of block copolymers have been developed and applied using conventional Ziegler-Natta catalysts. The processes include batch reactors and sequential additions techniques, series batch reactors, loop and tubular reactors, and fluidized bed reactors. A review of the processes and patents is given in chapter 4 of "Block Copolymers" [D. C. Allport and W. H. James; John Wiley and Sons, New York 1973]. In principle, the catalysts of this invention can be used in any of the processes described above for the production of well-defined block copolymers.

The most demanding process, that is the process which requires the longest chain lifetimes, is sequential addition. In the first step of the sequential addition process, the catalyst is placed in a well stirred batch reactor in a suitable solvent and first segment of the block copolymer is grown by adding a specific number of molar equivalents of monomer(s). The catalyst consumes all of the monomer(s) prior to addition of the second monomer(s) (a different set of monomers than in the first step). This procedure can be repeated to prepare multi-block copolymers. As an added step the polymerization vessel can be vacuumed free of substantially all leftover monomer or vented of monomer and/or purged with nitrogen or other suitable inert dry gases inbetween some or all of the monomer addition steps.

Sequential Addition Conditions: Solvent

Preferably, the solvent should normally disperse or dissolve the catalyst to form a well-mixed system. The most preferred catalysts for block copolymer synthesis, $(ACpHfMe(L'))[B(C_6F_5)_4]$, are prepared in toluene and form non-miscible, toluene-dispersable phases. The concentration of toluene in the catalyst phase depends on temperature and the structure of the catalyst. While aliphatic hydrocarbons, fluorinated hydrocarbons, and chlorinated aromatic hydrocarbons may be used in this invention, the preferred solvents for the preparation of block copolymers from the most preferred catalysts are aromatic hydrocarbons such as toluene, xylene, ethyl benzene and the like.

Temperature

The reactor temperature strongly affects the yield of block copolymer and must be adjusted depending on the type and concentration of monomers and catalyst used. The general procedure for determining this condition is to 1) find the maximum temperature where high molecular weight polymer segments can be prepared and 2) confirm the molecular weight is controlled by the catalyst-to-monomer ratio at this temperature. The general trend is that higher temperatures cause chain transfer to be more rapid relative to propagation and therefore give lower block copolymer yields. The process may be carried out at temperatures of $-80°$ C. to $80°$ C., however, it is preferred that the temperature be in the range of $-10°$ C. to $20°$ C.

Concentration of Catalyst

The concentration should be high enough to produce significant rates of polymerization under the generally low pressure conditions of sequential addition. The concentration should not be so high as to produce uncontrollable exotherms upon exposure to the monomer. The exotherm can be controlled, however, by adjusting the rate of monomer addition during the formation of a block segment. This level of control allows for a large range of acceptable catalysts concentrations. The process may be carried out at catalyst concentrations ranging from about $6 \times 10^{-6}$ to about $6 \times 10^{-2}$ moles of catalyst/liter of solution, however it is preferred that catalyst levels be in the range of $1 \times 10^{-4}$ to about $3 \times 10^{-3}$ moles of catalyst/liter of solution.

Monomer Concentration

The amount of monomer added depends on the molecular weight of the targeted polymer and the moles of active catalyst in the reactor. Molar ratios of monomer to catalyst may be in the range of about 10:1 to about 10,000:1. The monomers may be added quickly or may be metered in to the reactor to control exotherms.

Order of Monomer Addition

Precipitation of polymer (with catalyst attached) causes undesirable broadening of the molecular weight distribution due to mass transport limitations and poor mixing. It is therefore preferred to prepare the soluble block (generally the elastomeric segment) in the first stage of the reaction. Thus, as indicated in the examples, when ethylene is added in the first step in the synthesis of a HDPE-b-atactic-PP diblock copolymer the initially formed polyethylene precipitates with the catalyst and the final molecular weight distribution of crude block copolymer product is rather broad (Mw/Mn=3.0). Addition of propylene in the first step produces a system which remains homogenous throughout the block copolymer synthesis, yielding a crude product having a much narrower Mw/Mn=(1.7-1.8).

Method of Monomer Addition

Monomer may be added and removed in such a way that the resulting block copolymer has excellent properties, such as blocking efficiency. This is accomplished by applying a 5 to 10 psi ($\approx 34$ kPa to $\approx 69$ kPa) vacuum and purging the reactor with a dry inert gas, such as nitrogen, between monomer addition steps. In a preferred embodiment a minimum vacuum needed is about 5 psi. The dry inert gas purge may be at about 5 psi or above, preferably at or above about 15 psi even more preferably between about 5 and 25 psi in a two liter reactor. As is well known to those of ordinary skill in the art the pressures will vary with the size and other conditions of the reactor. Thus these numbers are a guide and not meant to be absolute.

Preparation of Tapered and Random Copolymers

Addition of stoichiometric amounts of a mixture of two olefins to the reactor under block copolymer conditions will naturally produce tapered copolymer because the monomers will generally have different reactivities with the catalyst. Thus, the head of the polymer will be rich in the more reactive comonomer while the polymer tail will contain larger amounts of the slower reacting comonomer. The extent of tapering will depend on magnitude of the difference of monomer reactivity. The extent of tapering can be controlled by metering the two monomers into the reactor at different rates.

Random copolymers such as non-crystalline ethylene-propylene rubber can be made under block copolymer conditions by adding the fast monomer (ethylene) to the catalyst/propylene mixture at a rate where the desired amount of ethylene has been added when all the propylene has been consumed. This procedure is exemplified for a ethylene-propylene elastomer containing 50 mole % propylene.

In a preferred embodiment, tapered block copolymers having properties typical of thermoplastic elastomers (TPE's) can be produced. These particular tapered block copolymers typically strong and elastic, having a low modulus at low strain, high tensile strengths, up to about 2500 psi or more, and a tension set of about 14 to about 25. These tapered copolymers are also characterized by an ethylene content of about 15 to about 25 mole %, preferrably about 18 to about 23 mole %. These tapered block copolymers can be produced by using a chiral hafnium catalyst, such as those used in the examples below, at a reaction temperature of about $-10$ degrees C. to about 20 degrees C., preferrably about $-5$ degrees C. to about 10 degrees C. However, higher temperatures could be used, depending on the heat dissipation system utilized. These tapered block copolymers apparently have long steroregular segments of crystalline polypropylene that are probably formed when the concentration of ethylene in the feed drops to a low level. The DSC melting curves of these polymers typically show a broad melting peak with a sharp crystallization peak at low temperatures.

Block Copolymer Products

The novel polymer products of this invention are olefinic block and tapered copolymers having narrow molecular weight distributions and well defined di-, tri-, multiblock or tapered structures. The polymer segments which can be incorporated into these architectures include 1) elastomers such as atactic polypropylene, atactic poly-1-olefins, and ethylene/1-olefin copolymers wherein the ethylene comonomer is a $C_3$-$C_{18}$ $\alpha$-olefin such as ethylene-propylene, ethylene butene, and ethylene-octene copolymers ethylene-propylene-diene terpolymers and other crosslinkable elastomeric olefins; 2) thermoplastics such as high density polyethylene, linear low density polyethylene having melting points from 80°-135° C. (e.g. ethylene-propylene and other ethylene-1-olefin copolymers wherein each 1-olefin has from about 4 to 20 carbon atoms), ethylene/diene copolymers such as ethylene/ethyldiene-norbornene copolymers, isotactic polypropylene having melting points from 100° C.–165° C., syndiotactic polypropylenes having melting points from 100° C.–165° C., semi-isotactic polypropylenes and other crystalline 1-olefin homo and copolymers; and 3) glasses such as homo-polycyclopentene, homopolynorbornene and the like. The average molecular weight of the polymer segments included in the novel block copolymers of this invention can be in the range of from 100–1,000,000 daltons, preferably from 30,000 to 200,000 daltons. The molecular weight distributions (Mw/Mn) of the crude and/or fractionated block copolymer are preferably about 5 or less, even more preferably about 3 or less, even more preferably 2.5 or less, and even more preferably about 2 or less. As indicated above and in the examples following the percentage of block copolymer in the crude product can vary from about 1% to 100%, preferably from about 50% to about 90% depending on the application and the conditions of the experiment. Furthermore, preferred block copolymers of this invention have blocking efficiencies of about 30% or greater, preferably about 50% or greater, more preferably about 70% or greater, even more preferably about 90% or greater, and most preferably about 95% or greater. In a preferred embodiment shorter reaction times and lower reactror temperatures are used to produce bolck copolymers having enhanced blocking efficiency.

The block copolymers of this invention can also be formulated into a wide variety of adhesives by blending the block copolymers with one or more solid or liquid tackifiers and optionally other known components such as oils, plasticizers, fillers, antioxidants, coloring agents, and the like. Useful tackifiers include natural rosins, hydrogenated or non-hydreogenated linear, branched or cyclic aliphatics or aromatics and mixtures thereof. The tackifiers may be present at from about 5 weight percent to about 95 weight percent based upon the weight of the composition. Fillers and other additives may be present at up to about 150 weight percent based upon the weight of the copolymer and the tackifiers.

The block copolymers may also be molded or shaped into articles such as bumpers, shoe soles, dash boards, automotive parts, containers, sheeting and the like by methods known in the art. Fillers and other additives known in the art, such as carbon black, silica, talc, glass, glass fibers, antioxidants, plasticizers, oils, waxes, coloring agents, and the like may further be added to the compositions before or after molding or shaping. The block copolymers can also be used in foams, sealants, coatings, weather strippings, sound absorbers and the like with the appropriate additives known to those of ordinary skill in the art, such as foaming agents, tackifiers, oils, plasticizers, films and the like.

The block copolymers of this invention can be represented by the following general formula:

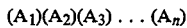

$(A_1)(A_2)(A_3) \ldots (A_n)$ wherein each A is a polymer segment having an average molecular weight from about 100 to about 1,000,000 daltons chosen independently from homopolymers consisting of HDPE, homo and copolymers of cyclic olefins, such as polycyclopentene and polynorbornene, and isotactic, atactic, and syndiotactic poly-1-olefins such as atactic-PP, isotactic-PP, syndiotactic-PP; random copolymers of 1-olefins and diolefins such as ethylene-propylene rubber, ethylene-propylene-hexadiene rubber, ethylene-butene rubber, linear low density polyethylenes, such that no adjacent segments are the same polymer composition.

Novel block copolymers of this invention include but are not limited to diblock copolymers such as (HDPE)-(EP), (i-PP)(EP), (LLDPE)(a-PP), (HDPE)(a-PP), (LLDPE)(HDPE) and the like, and triblock copolymers such as (HDPE)(EP)(HDPE), (HDPE)-(EP)(LLDPE), (LLDPE)(a-PP) (LLDPE), (HDPE)(a-PP)(LLDPE), (i-PP)(EP)(i-PP), (s-PP) (EP)(s-pp) and the like. It will be recognized to those well versed in the field that the isotactic polypropylene segments contained in the block copolymers of this invention have microstructure defects which are not observed in conventional i-PP materials prepared using titanium Ziegler-Natta catalyst. The microstructure defects which are unique to isotactic polypropylenes prepared using metallocene catalysts arise from 1–3 and 2–1 additions to propylene. The melting points of such materials can vary from 60° C. to 165° C. depending on the total number total defects.

The tapered copolymers can be represented by similar general formula where the transitions between idealized polymer segments $A_n$ are gradual. These gradient transitions between segments are represented by arrows.

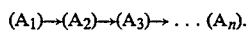

$(A_1) \rightarrow (A_2) \rightarrow (A_3) \rightarrow \ldots (A_n)$.

An example of this would be a polymer prepared by reacting a 50—50 mixture of ethylene and propylene with a living catalyst which has a high preference for ethylene over propylene. The tapered polymer obtained in such an experiment would be designated by the following formula:

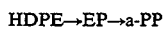

HDPE→EP→a-PP

The GPC data was obtained on a Waters 150 GPC instrument (MCL, Baytown) equipped with an RI detector. The samples were run at ca. 140° C. in trichlorobenzene solvent. The molecular weights were calculated from the PP calibration curves. The thermal behavior of the polymers was recorded by DuPont 912 Differential Scanning Calorimeter. The room temperature and the high temperature tensile properties of polymers were tested on Instron 4505. The polymers were compression molded on a Carver Press into thin sheets and allowed to condition for 24 hours. The micro-tensile specimens were cut and pulled at a crosshead speed of either 2 or 20 in/min. The samples were equilibrated for 5–10 minutes in an environmental chamber prior to testing for high temperature tensile properties. The tension set was measured in terms of % residual strain after holding the sample at 100% strain for 10 minutes followed by relaxation.

EXAMPLE 1

First Ethylene then Propylene

The reactor was cooled to 0° C. and charged with 400 mls of toluene and 0.20 mmoles of catalyst (bis cyclopentadienyl hafnium dimethyl and N,N, dimethylanilinium tetrakis(pentaflurophenyl)boron. Ethylene (4.0 grams; 0.143 moles) was added to 0° C. and 2 psig over 25 minutes. After all the ethylene was consumed, propylene (6 grams; 0.139 moles) was added; after 30 minutes the reactor was dropped and the product collected. The crude product contained 50 mole % propylene, had a $M_n = 87,000$ with a molecular weight distribution of 3.0. The crude product was washed with hexane at room temperature to remove any a-PP which was not in the form of block copolymer. The hexane insoluble material contained crystalline HPDE (as determined by IR) and 30 mole % propylene; the $M_n$ was 144,000 with a molecular weight distribution of 1.89. The hexane soluble fraction was a-PP, did not contain ethylene (by IR), and had a $M_n$ of 63,000 with a molecular weight distribution of 1.47. Based on the extraction studies, it was concluded that 50-60% of the a-PP chains were incorporated into a block copolymer under these conditions.

EXAMPLE 2

First Propylene then Ethylene

The procedure of Example 1 was repeated except propylene was added first. The crude product had 41 mole % propylene (IR), a $M_n$ of 170,000 with a molecular weight distribution of 1.78. A pad was pressed and extracted with hexane for 4 hours. At this point, the material contained 37 mole % propylene and very crystalline HDPE. The pad was further extracted with toluene at room temperature for 50 hours with no loss of weight. The extracted "diblock" had a $M_n$ of 230,000 and a molecular weight distribution of 1.48 (the hexane solubles were a-PP having a $M_n$ of 125,000 and a molecular weight distribution of 1.72).

EXAMPLE 3

Mw Control in Block Copolymer Synthesis

Using the procedure in Example 2, 3.0 grams of propylene (0.070 moles) were added to 0.20 mmole of the catalyst. After the propylene (0.071 moles) was completely consumed, 2.0 grams of ethylene were added to the system. The resulting product was washed with hexane at room temperature to remove any a-PP. The resulting block copolymer had a $M_n$ of 107,000 and a molecular weight distribution of 1.68, and contained 42 mole % propylene by IR spectroscopy.

EXAMPLE 4

Effect of Temperature

The procedure of Example 1 was followed except the temperature was varied. If the temperature is raised the effect is to lower the efficiency of the block formation. The temperature was raised from 0° C. to 10° C. and the blocking efficiency was reduced to less than 10%. When the temperature was lowered to −5° C., the blocking efficiency improved 78%.

EXAMPLE 5

Increasing Time Between Monomer Addition

A series of block copolymerizations were run at 0° C. and the time between the addition of propylene and ethylene was varied from 6 to 42 minutes. The crude products were collected, analyzed by GPC and IR, then extracted with hexane at room temperature for 65 hours to remove unblocked a-PP. In a well-behaved system wherein the extraction technique removes all of the a-PP, a logrithmically increase in the percent of hexane extractables with time would be expected. The data of this example is shown in FIG. 1 in graphical form. The Y-axis represents the percent of polypropylene which is incorporated into the block copolymer. The extractables were isolated and analyzed by GPC and IR; they were all pure a-PP. The correlation is close to the linear result expected so that this technique can be used to evaluate the kinetics of chain loss under a variety of conditions. This result confirms the ability to make true block copolymers, and confirms that hexane extraction is a good measure of block copolymer efficiency for this polymer system.

EXAMPLE 6

Preparation of EP

The procedure of Example 1 was followed except where noted. In this example, 1.6 grams of propylene (0.037 moles) were added to [Cp$_2$HfMe$_2$][B(pfp)$_4$] (0.30 mmole) in 400 cc of toluene at 0° C. Immediately after the propylene addition, 1.1 grams of ethylene (0.039 moles) was metered in over 3 minutes. After six minutes, the product was recovered yielding 2.7 grams of amorphous EP rubber. The product was non-crystalline by IR; the polymer had a $M_n$ of 96,000 and a molecular weight distribution of 1.69.

EXAMPLE 7

Preparation of EP

The procedure of Example 1 was followed except where noted. In this example 3.2 grams of propylene (0.074 moles) was added to [Cp$_2$HfMe$_2$][B(pfp)$_4$] (0.30 mmole) in 400 cc of toluene at 0° C. Ethylene (2.2 grams; 0.078 moles) was added to the reactor over 5.5 minutes. The product was recovered yielding 5.7 grams of EP rubber having a Mn of 155,000, and molecular weight distribution of 1.48. The IR showed some degree of PE-crystallinity.

EXAMPLE 8

Preparation of EP-b-HDPE

Example 6 was repeated to prepare "living" EP-rubber. After all the monomer had been consumed, ethylene (1.1 grams) was added to prepare the desired block copolymer. The product was recovered yielding 4.25 grams of copolymer. The IR showed PE crystallinity and the polymer had thermoplastic-like properties. The onset of Tg was −52.9° C. and the product had a melting point of 119° C. The $M_n$ of the crude product was 161,000 with a molecular weight distribution of 1.59.

EXAMPLE 9 aPP-HDPE di-Block Copolymer

Blocks were synthesized as follows:

To 400 ml. of toluene containing 0.29 mmoles of Cp$_2$Hf(Me)$_2$ DMA(B(pfp)$_4$), 2.3 g. of propylene was added first to a two liter zipperclave reactor at 0° C. (DMA(B(pfp)$_4$)=N,N-dimethylanilinium terakis (pentaflourophenyl) boron.) After 6 minutes of polymerization, the pressure dropped to approximately 1 psi. The reactor was then vented through a Nujol bubbler. A 5-6 psi vacuum was applied at the end of the PP reaction, followed by purging with 20 psi of N$_2$. 20 psi of N$_2$ was charged into the reactor while stirring and then vented to aid in removing any remaining propylene monomer dissolved in the solution. After venting N$_2$, 1.5 gm. of ethylene was added slowly and allowed 1-3 minutes for complete reaction. The resulting polymer was precipitated in the methanol and then extracted with hexane for 24 hours at room temperature. Soluble aPP was extracted by hexane whereas HDPE of aPP-HDPE block copolymer remained insoluble. Both hexane-soluble and insoluble species were then subjected to GPC and FTIR analysis for MW and composition. This vacuum/$N_2$ purging technique produced an end product with a high degree of HDPE formation. Characterization results are summarized in table 1.

Mechanical properties (tensile, elongation, and tension set) were also measured for the aPP-HDPE diblock copolymers made. All measurements were done on an Instron model 4505 with crosshead speed set at 20 inches/minute. Test conditions for the tension set measurements were as follows: 100% elongation for 10 minutes at room temperature, then released. Percent deformation was measured immediately and after 10 minutes.

TABLE 1

| aPP-HDPE Di-Block Copolymers | | | | | |
|---|---|---|---|---|---|
| Charge No. 17005- | 87-41 | 95-45 | 97-46 | 101-48 | 103-49 |
| Yield (gm) | 4.87 | 4.03 | 4.04 | 5.24 | 4.56 |
| Hexane Insolubles wt. % | 76 | 80 | 86 | 91 | 78 |
| PP content, wt. % | 36 | 44 | 57 | 49 | 43 |
| Modulus, psi | 1673 | 2150 | 2820 | 2467 | 2217 |
| Elongation, % | 602 | 400 | 382 | 567 | 476 |
| Tensile, psi | 1308 | 998 | 933 | 1345 | 1134 |
| Tension Set, % | — | 46 | 57 | 53 | 59 |
| Tm, °C. | 107 | 108 | 117 | 119 | 116 |
| $M_n$, × 1000 | 218 | 295 | 245 | 255 | 239 |
| $M_w/M_n$ | 1.35 | 1.61 | 1.54 | 1.93 | 1.69 |
| Hexane Solubles | | | | | |
| $M_n$, × 1000 | — | 114 | 101 | 112 | 102 |
| $M_w/M_n$ | — | 1.76 | 1.72 | 2.12 | 1.6 |
| % $C_3^=$ as aPP | 47 | 36 | 22 | 17 | 40 |
| Cat. Activity | | | | | |
| Mole Di-block/mole cat. | 0.059 | 0.038 | 0.0049 | 0.065 | 0.051 |
| Mole aPP/mole cat. | — | 0.025 | 0.019 | 0.014 | 0.034 |
| Active cat. Mole % | — | 6.3% | 6.8% | 7.9% | 8.5% |

EXAMPLE 10

HDPE-aPP-HDPE Tri-Blocks

Synthesis of tri-block copolymers was performed under the same conditions as Example 9. In order to avoid precipitation of the first HDPE block in the toluene solution, a small amount of gas phase $C_3^=$ was charged into the reactor and polymerized prior to adding the first block $C_2^=$ monomer. We applied 10 psi vacuum, followed with a 20 psi $N_2$ purge between each monomer sequence before addition of a new monomer. The final products were precipitated in methanol and dried in a vacuum oven. In order to analyze the product composition, samples were extracted in hexane for 24 hours at room temperature. Block copolymers of HDPE-aPP or HDPE-aPP-HDPE would remain insoluble, whereas aPP would be extracted in this solvent. All soluble as well as insoluble samples were then subjected to MW and compositional analysis by GPC and FTIR. The results for total yields, weight percent of hexane extraction, MW and propylene content are summarized in the following table 2.

TABLE 2

| HDPE-aPP-HDPE Tri-block Copolymers | | | |
|---|---|---|---|
| | Reac. I (17005-159) | Reac. II (17005-161) | Reac. III (17005-163) |
| Total Yield (gm) | 2.41 | 6.97 | 9.03 |
| Hexane insoluble wt % | 95 | 59 | 92 |
| Propylene content, wt % | 25.8 | 51.9 | 50.4 |
| Modulus, psi | — | 2157 | 2444 |
| Elongation, % | — | 670 | 638 |
| Tensile, psi | — | 2398 | 2256 |
| Tension set, % (10 min at 100%) | — | 28 | 32 |
| $M_n$, (× $10^{-3}$) | 125 | 346 | 331 |
| $M_w/M_n$ | 2.1 | 1.8 | 2.1 |
| Hexane Soluble | | | |
| $M_n$ (× $10^{-3}$) | — | 121 | 115 |
| $M_w/M_n$ | — | 2.4 | 3.1 |

Results of FTIR analysis show that all of the hexane soluble are 100% aPP.

In order to assess the mechanical properties of the linear tri-block copolymers, we synthesized six more samples according to the same reaction conditions as previously described. Table 3 summarizes the data. Samples #51, #53 and #54 were run with block ratios of 1:3:1. Samples #55, #56 and #52 were run with a block ratio of 1:6:1. Sample #52 was run with twice the amount of monomers charged and with the same level of catalyst concentration. We obtained a Mn=306,000 (almost double) with a similar narrow Mw/Mn=2.0.

TABLE 3

| HDPE-aPP-HDPE Tri-Block Copolymers | | | | | | |
|---|---|---|---|---|---|---|
| Block Ratio | 1:3:1 | | | 1:6:1 | | |
| Charge No. | 51 | 53 | 54 | 55 | 56 | 52 |
| Total Yield (gm) | 8.87 | 9.15 | 8.95 | 7.43 | 7.44 | 13.19 |
| Hexane Insolubles, wt. % | 86 | 79 | 72 | 41 | 47 | 71 |
| PP content, wt. % | 56 | 64 | 60 | 80 | 74 | 59 |
| Modulus, psi | 1821 | 1567 | 2607 | 859 | 1243 | 2933 |
| Elongation, % | 676 | 737 | 723 | 810 | 930 | 629 |
| Tensile, psi | 1630 | 1638 | 2039 | 1198 | 1625 | 2171 |
| Tension Set, % | 36 | 24 | 28 | 25 | 19 | 33 |
| Tm, °C. | 134 | 119 | 121 | 110/137 | 119 | 129 |
| $M_n$, × 1000 | 287 | 293 | 270 | 241 | 207 | 306 |
| $M_w/M_n$ | 1.9 | 1.9 | 1.9 | 1.9 | 1.9 | 2.0 |
| Mole. polymer chain/mole. cat. | 0.09 | 0.09 | 0.08 | 0.04 | 0.06 | 0.11 |
| Hexane Solubles | | | | | | |
| $M_n$, × 1000 | 171 | 206 | 197 | 222 | 192 | 207 |
| $M_w/M_n$ | 2.0 | 2.0 | 1.9 | 2.1 | 2.0 | 1.9 |
| Mole. polymer chain/mole. cat. | 0.03 | 0.03 | 0.04 | 0.07 | 0.07 | 0.06 |
| Mole % Active Cat. | 0.12 | 0.12 | 0.12 | 0.11 | 0.13 | 0.17 |

EXAMPLE 11

HDPE-EP-HDPE Tri-block Copolymers

The procedure set out in Example 9 was followed. Three reactions were run with each reaction being terminated at the end of each blocking sequence. Samples of the hexane-soluble and insoluble fractions for each of these reactions were subjected to MW and compositional analysis by GPC and FTIR. Table 4 below summarizes the results.

TABLE 4

| Reactions | I | II | III |
|---|---|---|---|
| Total Yields (g) | 2.06 | 9.06 | 9.80 |
| Mn ($\times 10^{-3}$) | 237 | 190 | 299 |
| Mw/Mn | 2.05 | 2.70 | 2.19 |
| Hexane Insoluble | | | |
| Wt % | 99.6 | 36.2 | 51.8 |
| PP Content, wt % | 5.4 | * | * |
| Mn ($\times 10^{-3}$) | 189 | 324 | 297 |
| Mw/Mn | 2.28 | 1.94 | 2.37 |
| Hexane Solubles** | | | |
| Wt % | 0.4 | 63.8 | 48.2 |
| Mn ($\times 10^{-3}$) | — | 164 | — |
| Mw/Mn | — | 2.44 | — |

*The FTIR PP content was too high to be accurately calculated.
**FTIR shows hexane solubles contain both aPP and EP.

Three additional reactions were run using the same reaction conditions as previously described but varying the block ratio and the middle block E/P composition. Table 5 summarizes results from these runs.

TABLE 5

HDPE-EP-HDPE Block Copolymers
(same reaction conditions as in Example 1)

| Charge No. 17005- | 125-57 | 127-58 | 129-59 |
|---|---|---|---|
| Block Ratio, by wt. | 1:2.5:1 | 1:3.6:1 | 1:13:1 |
| E/P Ratio, by wt. | 1:1 | 1:6 | 1:12 |
| Total Yield, g | 7.2 | 8.2 | 13.6 |
| Exotherm, °C. | 1 | 5 | 20 |
| Hexane Insolubles | | | |
| Wt % | 97 | (30) | 36 |
| Propylene content, wt % | 45.9 | 85.2 | — |
| Modulus, psi | 1560 | 3107 | 550 |
| Elongation, % | 509 | 290 | 885 |
| Tensile, psi | 1046 | 1204 | 688 |
| Tension set, % (10;, 100%) | 26 | 45 | 46 |
| Mn (K) | 510 | 544 | 156 |
| Mw/Mn | 1.8 | 2.1 | 3.4 |
| Mol. polymer/ Mol. catalyst | 0.047 | 0.016 | 0.108 |
| Hexane Solubles | | | |
| Wt % | 3 | 70 | 64 |
| Mn, 1000 | 309 | 470 | 121 |
| Mw/Mn | 2.0 | 2.3 | 4.1 |
| Mol. polymer/ Mol. catalyst | 0.0024 | 0.042 | 0.248 |

EXAMPLE 12

EP-RCP Block Copolymers

Sequential monomer addition technique was used to synthesize (A) EP-b-RCP Block Copolymers and (B) EP-b-iPP Block Copolymers. (RCP is a tapered or randon copolymer of propylene and an alpha olefin preferrably ethylene. In the tapered RCP, the polymer chain is amorphous in one end and gradually becomes semi-crystalline toward the other end.) Removal of the residual ethylene of the "EP" block by vacuum technique was used to synthesize EP/PP block copolymers consisting of isotactic "PP" block and tapered copolymers (147-1,149-1, 150-1). The catalyst used was Me-Si$_2$(bis-indeneyl) hafnium dimethyl, indicated in the tables as "Hf-*", with DMAH(B(pfp)$_4$).

The procedure of example 9 was used except where noted. The polymerization runs were carried out in a 1 L autoclave reactor using toluene diluent. The "EP" block was formed first followed by the "PP" block. In between monomer addition steps the reactor was vented completely (0 psi pressure) or subjected to vaccum/nitrogen purge cycle. The yield was determined by completely drying the crude product in the vacuum oven at 100° C. for at least 24 hours. The crude product was then subjected to heptane extraction at RT/50° C. for 24 hours. The heptane soluble fraction is the unblocked EP copolymer and heptane insoluble part is EP-b-PP block copolymer.

A. Synthesis and Characterization of EP-block-RCP (Random Co-Polymer)

Sequential monomer addition technique was employed. "EP" block was formed first followed by the "PP" block. The reactor was vented inbetween monomer addition steps. The details of the polymerization conditions and the characterization data of block copolymers are reported in Table 7. A control "EP" run was carried out under similar conditions to simulate "EP" block of EP/PP block copolymer. The crude product obtained in the block run was subjected to the heptane extraction at room temperature.

(B) Synthesis and Characterization of EP-block-iPP

We followed the procedure in Example 12A above, however, by applying vacuum in between the "EP" and "PP" block, we were able to remove the residual C$_2$ of "EP" block. The resultant block copolymers exhibited a sharp melting peak in the range of 135°–138° C. corresponding to the "iPP" block. The polymerization conditions and the characterization of EP-b-ipp block copolymers and tapered copolymers are reported in Table 8 and A. The crude product formed in the block run was subjected to heptane extraction at 50° C. to insure complete removal of the unblocked EP copolymer. The heptane insoluble fraction was considered to be the block copolymer. The wt % EP in the block copolymer is calculated from the results obtained in the heptane extraction studies. Mechanical properties are listed in tables 9 and 10.

TABLE A

| ID # | Mole % C$_2$ In Feed | Polymzn. Temp. (°C.) | Polymzn. Time (min.) | Conv. % | Hep. Sol. at RT (Wt %) | Mole % C$_2$ In Polymer (H NMR) | Mn/MWD (by GPC) | CI (PP) (by FTIR) |
|---|---|---|---|---|---|---|---|---|
| 16768-147-1 | 28 | 27 to 40 | 3.0 | 100 | 68.0 | 24 | 38.4 K/2.9 | 0.36 |
| 16768-149-1 | 28 | 0 to 10 | 1.5 | 100 | 28.0 | 22 | 93.8 K/1.8 | 0.41 |
| 16768-150-1 | 25 | −5 to 5 | 1.5 | 100 | 27.0 | 20 | 95.8 K/1.7 | 0.38 |
| 16768-156-1 | 33.3 | 26 to 27 | 5.0 | 100 | 100 | 30 | 80.5 K/1.7 | 0.1 |
| 17450-8-1 | 33.3 | 8 to 9 | 10.0 | 76 | 100 | 34.8 | 98.8 K/1.6 | 0.12 |
| 17450-26-1 | 33.3 | 6 to 8 | 2.0 | 89 | 100 | 32 | 91.4 K/1.6 | 0.1 |

Conditions: Hf-*/DMAH-B(pfp)$_4$ = 0.5 × 10$^{-4}$ − 1.0 × 10$^{-4}$ moles

TABLE 7

Synthesis Conditions and Characterization of EP-block-RCP
Conditions: [Hf-*] = 1.25 × 10$^{-4}$ M
[DMAH-B(pfp)$_4$] = 1.25 × 10$^{-4}$ M

| ID # | Run Type | Feed Comp. EP Block (Molar) [C$_2$] | [C$_3$] | C$_3$ Conc. PP Block (Molar) | Polymzn. Time (min.) EP | PP | Polymzn. Temp. (°C.) EP | PP | Conv. % | Wt % RCP | Mn/MWD | MP (°C.) |
|---|---|---|---|---|---|---|---|---|---|---|---|---|
| 146-1 | EP-PP | 0.33 | 0.825 | 0.413 | 1.0 | 2.0 | 27 to 41 | 35 | 100 | | 35 K/4.2 | |
| 146-2 | Hep Sol. (7 wt %) | | | | | | | | | | 27.3 K/3.9 | |
| 146-3 | Block (Hep Insol) | | | | | | | | | 30 | 65 K/2.3 | 126 |
| 147-1 | EP | 0.33 | 0.825 | | 3.0 | | 27 to 40 | | 100 | | 38.4 K/2.9 | |
| 148-1 | EP-PP | 0.33 | 0.825 | 0.413 | 1.5 | 6.0 | 0 to 7 | 7 | 92.4 | | 104.6 K/2.1 | |
| 148-2 | Hep Sol. (10 wt %) | | | | | | | | | | 31.4 K/3.5 | |
| 148-3 | Block (Hep Insol) | | | | | | | | | 25 | 125 K/2.0 | 130 |
| 149-1 | EP | 0.33 | 0.825 | | 1.5 | | 0 to 10 | | 100 | | 93.8 K/1.8 | |
| 151-1 | EP-PP | 0.33 | 0.975 | 0.33 | 1.5 | 3.0 | −5 to 5 | 5 | 100 | | 115.3 K/1.7 | |
| 151-2 | Hep Sol. (8 wt %) | | | | | | | | | | 59.4 K/2.0 | |
| 151-3 | Block (Hep Insol) | | | | | | | | | 25 | 128 K/1.6 | 120 |
| 150-1 | EP | 0.33 | 0.975 | | 1.5 | | −5 to 5 | | 100 | | 95.8 K/1.7 | |

TABLE 8

Synthesis Conditions (Vaccum Technique Used) and Characterization of EP-block-iso-PP
Conditions: [Hf-*] = 1.0 × 10$^{-4}$ moles
[DMAH-B(pfp)$_4$] = 1.0 × 10$^{-4}$ moles

| ID # | Run Type | Feed Comp. EP Block (Molar) [C$_2$] | [C$_3$] | C$_3$ Conc PP Block (Molar) | Polymzn. Time (min.) EP | PP | Polymzn. Temp. (°C.) EP | PP | Conv. % | Hep. Sol. @ 50C | Wt % EP (Extrn) | Mn/MWD | MP (°C.) |
|---|---|---|---|---|---|---|---|---|---|---|---|---|---|
| 14-1 | EP-PP | 0.66 | 0.33 | 0.66 | 6 | 6 | 1 to 10 | 9 | 100 | | | 126 K/2.3 | |
| 14-2 | Hep Sol. | | | | | | | | | 40% | | 124 K/2.2 | |
| 14-3 | Block (Hep Insol) | | | | | | | | | | 26 | 265 K/2.2 | 137 |
| 15-1 | EP | 0.66 | 0.33 | | 6 | | −1 to 7 | | 100 | 100% | | 91 K/1.7 | |
| 17-1 | EP-PP | 0.33 | 0.165 | 0.66 | 6 | 4 | 12 to 15 | 14 | 100 | | | 134 K/2.4 | |
| 17-2 | Hep Sol. | | | | | | | | | 20% | | 106 K/2.4 | |
| 17-3 | Block (Hep Insol) | | | | | | | | | | 22 | 344 K/2.1 | 138 |
| 19-1 | EP | 0.44 | 0.22 | 0.66 | 6 | 4 | 6 to 8 | 8 | 93 | | | 143 K/2.6 | |
| 19-2 | Hep Sol. | | | | | | | | | 28% | | 78 K/1.7 | |
| 19-3 | Block (Hep Insol) | | | | | | | | | | 30 | 224 K/2.0 | 137 |
| 26-1 | EP | 0.44 | 0.22 | | 2 | | 6 to 8 | | 90 | 100% | | 92 K/1.6 | |
| 24-1 | EP-PP | 0.88 | 0.44 | 0.66 | 3.5 | 6 | 6 to 14 | 14 | 88 | | | 78 K/2.3 | |
| 24-2 | Hep Sol. | | | | | | | | | 47% | | 69 K/2.1 | |
| 24-3 | Block (Hep Insol) | | | | | | | | | | 49 | 125 K/1.7 | 135 |
| 25-1 | EP | 0.88 | 0.44 | | 1.5 | | 5 to 13 | | 100 | 100% | | 78 K/1.9 | |
| 29-1 | EP-PP | 0.88 | 0.44 | 1.1 | 4 | 6 | 0 to 8 | 8 to 10 | 100 | | | 97 K/3.1 | |
| 29-2 | Hep Sol. | | | | | | | | | 21% | | 84 K/3.0 | |
| 29-3 | Block (Hep Insol) | | | | | | | | | | 37 | 218 K/3.2 | 138 |
| 15-1 | EP | 0.66 | 0.33 | | 6 | | −1 to 7 | | 100 | 100% | | 91 K/1.7 | |
| 30-1 | EP-PP | 0.44 | 0.22 | 0.66 | 3 | 5 | 6 | 6 | 35 | | | 120 K/2.9 | |
| 30-2 | Hep Sol. | | | | | | | | | 35% | | 82 K/1.8 | |
| 30-3 | Block (Hep Insol) | | | | | | | | | | | 241 K/1.9 | 137 |

TABLE 9

| ID # | Stress @ Yield (psi) | % Strain @ Yield | Tensile Strength (psi) | % Strain @ Break | Toughness (in-lb/in$^3$) |
|---|---|---|---|---|---|
| 14-3 | 2,364 | 17 | 4,221 | 714 | 18,220 |
| 17-3 | 2,883 | 16 | 3,264 | 526 | 12,160 |
| 19-3 | 3,264 | 13 | 5,115 | 714 | 22,230 |
| 24-3 | 1,931 | 19 | 3,900 | 774 | 17,660 |
| 29-3 | 3,051 | 16 | 4,489 | 700 | 19,310 |
| isoPP Mn = 237K MWD = 2.16 | 3,688 | 12 | 3,440 | 470 | 12,100 |

TABLE 10

| ID # | 100% Modulus (psi) | 300% Modulus (psi) | Tensile Strength (psi) | % Strain @ Break | % Recovery After 100% Strain |
|---|---|---|---|---|---|
| 147-1 | 268 | 333 | 1,500 | 1,320 | 90 |
| 149-1 | 469 | 558 | 1,587 | 870 | 85 |
| 150-1 | 427 | 503 | 1,750 | 1,035 | 85 |
| 146-3 | 859 | 979 | 2,734 | 822 | 60 |
| 148-3 | 983 | 1,127 | 2,616 | 726 | 55 |
| 151-3 | 961 | 1,100 | 3,100 | 788 | 55 |

We claim:

1. A process for producing block or tapered copolymers having an Mw/Mn of about 3 or less, an Mw between about 100,000 to about 1,000,000, and a blocking efficiency of about 50% or more comprising the steps of:

(i) contacting under polymerization conditions in a polymerization reactor a first olefinic monomer(s) with an activated catalyst complex which is the reaction product of:

(a) a cyclopentadienyl Group IVB metal component, and (b) a second component of an alumoxane or a compatible non-coordinating anion to produce a first living polymer; and (ii) sequentially adding to said living polymer at least a second olefinic monomer(s) to copolymerize with said first polymer to produce a block or tapered copolymer.

2. The process of claim 1 wherein the polymerization is vented or purged with a dry gas in between steps (i) and (ii).

3. The process of claim 1 wherein the polymerization reactor is vented or subjected to a vacuum and purged with a dry gas inbetween steps (i) and (ii).

4. The process of claim 1, 2 or 3 wherein the block copolymer is a diblock copolymer.

5. The process of claim 1, 2 or 3 wherein the block copolymer is a triblock.

6. The process of claim 2 or 3 wherein the block copolymer comprises isotactic PP blocks.

7. The process of claim 1 wherein the activated catalyst complex product is represented by the formulae:

[A-CpMX$_1$][(C$_2$B$_9$H$_{11}$)$_2$Co]

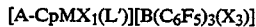

[A-CpMX$_1$(L')][B(C$_6$F$_5$)$_3$(X$_3$)]

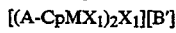

[(A-CpMX$_1$)$_2$X$_1$][B']

wherein: M is titanium, zirconium or hafnium; (A-Cp) is either (Cp)(Cp*) or Cp-A'-Cp; and Cp and Cp* are the same or different substituted or unsubstituted cyclopentadienyl radicals; A' is a covalent bridging group containing a Group IV-A element; L' is a neutral Lewis base; X$_1$ is a hydride radical, hydrocarbyl radical having from 1 to about 20 carbon atoms, substituted-hydrocarbyl radical, wherein 1 or more of the hydrogen atoms are replaced with a halogen atom, having from 1 to about 20 carbon atoms, or organo-metalloid radical comprising a Group IV-A element wherein each of the hydrocarbyl substituents contained in the organo portion of said organo-metalloid, independently, contain from 1 to about 20 carbon atoms; X$_3$ is a hydride, halide, hydrocarbyl radical, a C$_1$-$_{C20}$ hydrocarbyl radical wherein one or more of the hydrogen atoms is replaced by a halogen atoms, organometalloid radical wherein each hydrocarbyl substitution in the organ portion contains from 1 to 20 carbon atoms and the metal is a Group IVA metal and B' is a noncoordinating anion.

8. The process of claim 1, wherein the catalyst is the reaction product bis(cyclopentadienyl) hafnium dimethyl and N,N-dimethylanilinium terakis(pentaflouropheny)boron.

9. The process of claim 1 wherein said steps (i) and (ii) are carried out at a temperature of from about $-5°$ C. to about $10°$ C.

10. The process of claim 1 wherein any of said monomers is selected from the group consisting of ethylene, propylene, and 1-butene.

11. The process of claim 1 wherein the block or tapered copolymer has an Mn between about 38,000 and 550,000.

* * * * *